Figure 1:
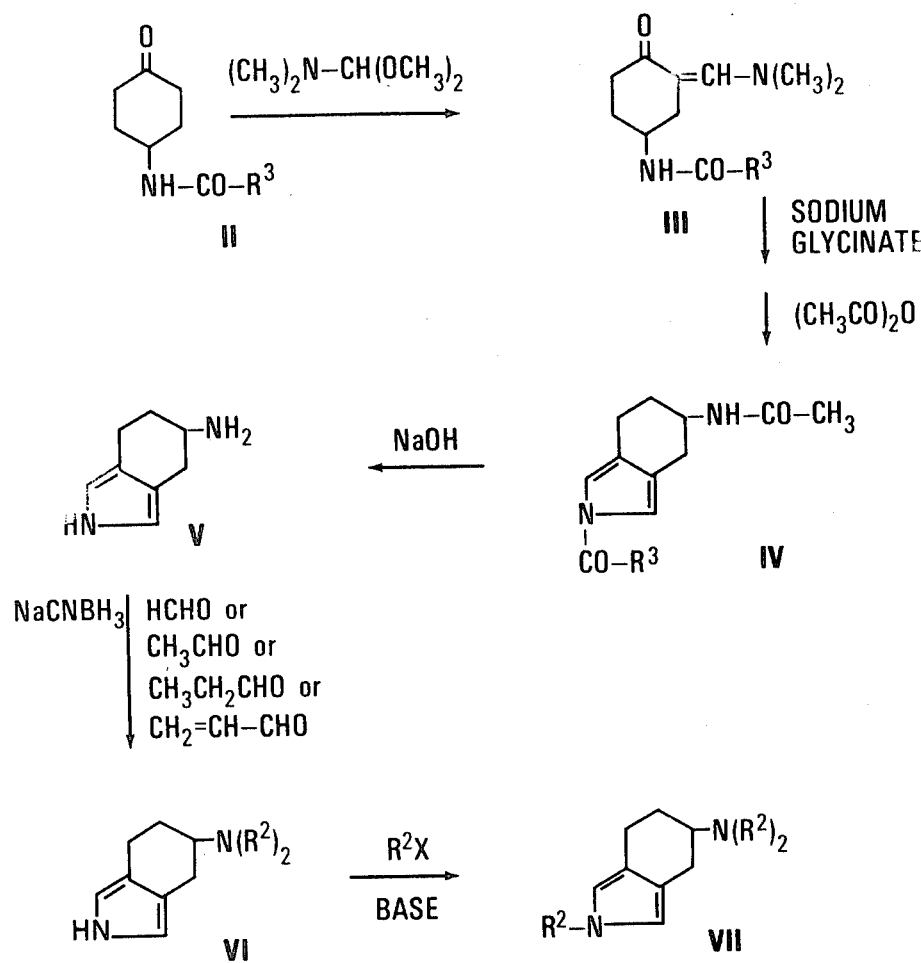
Figure 2:
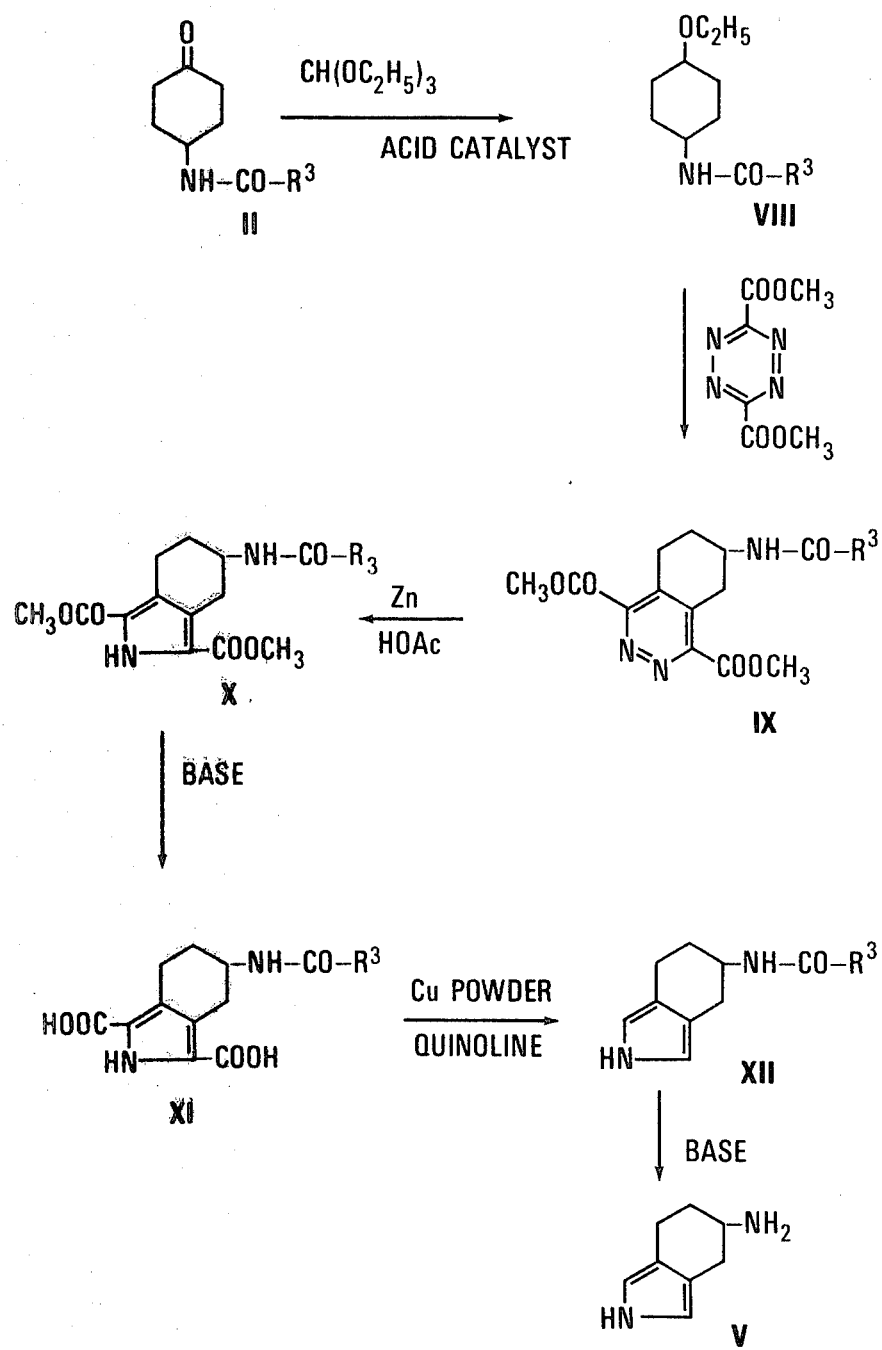

United States Patent [19]

Kornfeld et al.

[11] 4,235,776
[45] Nov. 25, 1980

[54] TETRAHYDRO-2H-BENZO[C]PYRROLES

[75] Inventors: Edmund C. Kornfeld; Nicholas J. Bach, both of Indianapolis, Ind.

[73] Assignee: Eli Lilly and Company, Indianapolis, Ind.

[21] Appl. No.: 20,560

[22] Filed: Mar. 15, 1979

Related U.S. Application Data

[63] Continuation-in-part of Ser. No. 5,063, Jan. 22, 1979, abandoned.

[51] Int. Cl.³ .................... C07D 209/44; A61K 31/40
[52] U.S. Cl. .................................. 260/326.1; 424/274
[58] Field of Search ...................... 260/326.1; 424/274

[56] References Cited

FOREIGN PATENT DOCUMENTS 943213  6/1965  France ................................. 260/326.1
1019111 2/1966  United Kingdom ................ 260/326.1

Primary Examiner—Donald G. Daus
Assistant Examiner—M. C. Eakin
Attorney, Agent, or Firm—James L. Rowe; Arthur R. Whale

[57] ABSTRACT

Tetrahydro-2H-benzo[c]pyrroles, useful as dopamine agonists, particularly as inhibitors of prolactin secretion and in treatment of Parkinson's syndrome.

9 Claims, 2 Drawing Figures

REACTION SEQUENCE I

TETRAHYDRO-2H-BENZO[C]PYRROLES

CROSS-REFERENCE

This application is a continuation-in-part of our copending application Ser. No. 5,063 filed Jan. 22, 1979 now abandoned.

SUMMARY OF THE INVENTION

This invention provides substituted dl-4,5,6,7-tetrahydro-2H-benzo[c]pyrroles of the following structure

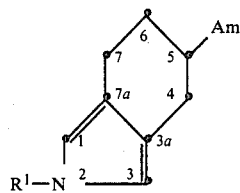

wherein $R^1$ is H,

or $R^2$, Am is $NH_2$ or $N(R^2)_2$ wherein $R^3$ is methyl, ethyl or n-propyl and each $R^2$ is independently $R^3$ or allyl, except that $R^1$ is not

when Am is $NH_2$ and acid addition salts thereof. Compounds according to I in which Am is

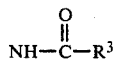

and $R^1$ is H,

or $R^2$ wherein $R^2$ and $R^3$ have the same meaning as hereinabove are included within the scope of this invention. They do not form salts.

Compounds according to Formula I wherein Am is either $NH_2$ or

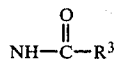

or those wherein $R^1$ is

are useful chiefly as intermediates whereas those in which Am is $N(R^2)_2$ are useful as dopamine agonists including their use in treating Parkinson's Syndrome and as prolactin inhibitors.

The pharmaceutically-acceptable acid addition salts of the compounds of this invention wherein $R^1$ is H or $R^2$, Am is $N(R^2)_2$ and $R^2$ is methyl, ethyl, n-propyl or allyl, include salts derived from non-toxic inorganic acids such as: hydrochloric acid, nitric acid, phosphoric acid, sulfuric acid, hydrobromic acid, hydriodic acid, nitrous acid, phosphorous acid and the like, as well as salts derived from non-toxic organic acids such as aliphatic mono and dicarboxylic acids, phenyl-substituted alkanoic acids, hydroxy alkanoic and alkandioic acids, aromatic acids, aliphatic and aromatic sulfonic acids, etc. Such pharmaceutically-acceptable salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, fluoride, acetate, propionate, decanoate, caprylate, acylate, formate, isobutyrate, caprate, heptanoate, propiolate, oxalate, malonate, succinate, suberate, sebacate, fumarate, maleate, mandelate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, β-hydroxybutyrate, glycollate, malate, tartrate, methanesulfonate, propanesulfonate, naphthalene-1-sulfonate, naphthalene-2-sulfonate and the like salts.

Acid addition salts of those intermediate compounds of this invention capable of forming salts which are those compounds according to Formula I wherein $R^1$ is H or $R^2$, Am is $NH_2$, and $R^2$ is methyl, allyl, ethyl or n-propyl, are not restricted to those formed with non-toxic anions since the chief use of such salts is for isolation and purification of the intermediates involved.

Illustrative compounds coming within the scope of Formula I above include:
dl-5-dimethylamino-4,5,6,7-tetrahydro-2H-benzo[c]pyrrole methane sulfonate.
dl-2-methyl-5-diethylamino-4,5,6,7-tetrahydro-2H-benzo[c]pyrrole maleate.
dl-5-diallylamino-4,5,6,7-tetrahydro-2H-benzo[c]pyrrole sulfate.
dl-2-ethyl-5-di(n-propyl)amino-4,5,6,7-tetrahydro-2H-benzo[c]pyrrole hydrochloride.
dl-2-crotonyl-5-acetamido-4,5,6,7-tetrahydro-2H-benzo[c]pyrrole.
dl-5-acetamido-4,5,6,7-tetrahydro-2H-benzo[c]pyrrole.
N,N,2-trimethyl-dl-5-amino-4,5,6,7-tetrahydro-2H-benzo[c]pyrrole.
N-methyl-N-allyl dl-5-amino-4,5,6,7-tetrahydro-2H-benzo[c]pyrrole.
dl-2-allyl-5-dimethylamino-4,5,6,7-tetrahydro-2H-benzo[c]pyrrole.
dl-2-propionyl-5-propionamido-4,5,6,7-tetrahydro-2H-benzo[c]pyrrole.
N-methyl-N-ethyl-dl-5-amino-4,5,6,7-tetrahydro-2H-benzo[c]pyrrole.
N-methyl-N-n-propyl-dl-2-methyl-5-amino-4,5,6,7-tetrahydro-2H-benzo[c]pyrrole.
N-allyl-N-n-propyl-dl-5-amino-4,5,6,7-tetrahydro-2H-benzo[c]pyrrole.

While the compounds represented by Formula I have been named as 4,5,6,7-tetrahydro-2H-benzo[c]pyrroles, an alternative name can be used; i.e., the compounds can be named as 4,5,6,7-tetrahydroisoindoles.

The presence of a substituent at C-5 in the benz[c]pyrrole or isoindole ring introduces a center of assymmetry into those molecules. Thus, compounds represented by Formula I include two optical isomers occurring as a dl pair or racemate. Resolution of a dl pair of this invention into its optical antipodes can be accomplished by procedures known to those skilled in the art.

The compounds of this invention containing an amino group (Am) at C-5 in the tetrahydro-2H-benzo-[c]pyrrole ring system can be prepared by at least two different procedures. The first of these is illustrated in Reaction Sequence I.

According to Reaction Scheme I, 4-acetamido cyclohexanone, prepared by the procedure of Fraser and Swingle, *Can. J. Chem.*, 48, 2065 (1970) is reacted with the dimethylacetal of dimethylformamide to yield 2-dimethylaminomethylene-4-acetamidocyclohexanone (III). Reacting this compound with sodium glycinate followed by a ring closure reaction in the presence of acetic anhydride yields, when $R^3$ is methyl, dl-2-acetyl-5-acetamido-4,5,6,7-tetrahydro-2H-benzo[c]-pyrrole (IV). Treatment of this latter compound with base gives dl-5-amino-4,5,6,7-tetrahydro-2H-benzo[c]pyrrole (V). This latter compound can be preferentially alkylated on the amino group at C-5 using a reductive alkylation procedure; i.e., reaction with an aldehyde (formaldehyde, acetaldehyde, acrolein, or propionaldehyde) in the presence of a strong organometallic reducing agent such as sodium cyanoborohydride. The dialkylated compound, for instance, dl-5-di(n-propyl)amino-4,5,6,7-tetrahydro-2H-benzo[c]pyrrole (VI) can also be alkylated on the pyrrole ring nitrogen under basic conditions using an alkyl halide $R^2X$ (methyl iodide, allyl chloride, ethyl bromide, or the like) to yield a dl-2-($C_1$-$C_3$ alkyl or allyl)-5-disubstituted-amino-4,5,6,7-tetrahydro-2H-benzo[c]pyrrole of Formula VII.

Other methods of alkylation of the amine groups at C-5 can be employed in addition to the reductive alkylation procedure illustrated above for converting V to VI. For example, direct alkylation with an alkyl halide, particularly an iodide, followed by a reaction of the thus-formed secondary amine with a suitable acyl halide; i.e., acetyl chloride or crotyl chloride followed by reduction again with an organometallic reducing agent, yields a 5-dialkylamino compound. This latter procedure particularly lends itself to the preparation of unsymmetrically substituted amine groups at C-5.

A second synthetic procedure is available for preparing the compounds of this invention as illustrated in Reaction Sequence II.

According to Reaction Sequence II, the same starting material 4-acylamidocyclohexanone, is employed as in Reaction Sequence I. The reaction of this starting material with ethyl orthoformate in the presence of an acid catalyst such as p-toluene sulfonic acid produces an enol ether; i.e., 4-acetamido-1-ethoxycyclohexene (VIII). Reaction of this derivative with 1,2,4,5-tetrazine dicarboxylic acid, dimethyl ester [prepared by the procedure of Sauer, et al. *Chem. Ber.*, 98, 1435 (1965)] yields a pyridazine diester (IX). Reduction of this diester with zinc in acetic acid or other suitable metal-acid reducing system causes a ring contraction to yield dl-1,3-dicarbomethoxy-5-acetamido-4,5,6,7-tetrahydro-2H-benzo[c]pyrrole (X). Selective hydrolysis of the diester with base yields the corresponding dicarboxylic acid (XI) which, on decarboxylation with copper powder in the presence of quinoline, gives dl-5-acetamido-4,5,6,7-tetrahydro-2H-benzo[c]pyrrole (XIII). Hydrolysis under basic conditions of the acyl group then yields the free amine, dl-5-amino-4,5,6,7-tetrahydro-2H-benzo[c]pyrrole (identical to compound V from Reaction Sequence I). Other acyl protecting groups can be used in the 4-acylamido cyclohexanone starting material besides acetyl including propionyl, butyryl and isobutyryl as well as benzoyl, dinitrobenzoyl, phenylacetyl and the like.

This invention is further illustrated by the following examples:

EXAMPLE 1

PREPARATION OF DL-5-AMINO-4,5,6,7-TETRAHYDRO-2H-BENZO[c]PYRROLE

A reaction mixture was prepared from 15.5 g. of 4-acetamidocyclohexanone [prepared by the procedure of Fraser and Swingle, *Can. J. Chem.*, 48, 2065 (1970)], 80 g. of the dimethylacetal of dimethylformamide, 1.5 ml. of triethylamine and 500 ml. of benzene. The benzene was distilled therefrom over a 1.5 hour period until the volume was reduced to about ⅓ of the original volume. An additional 250 ml. of benzene were added. The reaction mixture was heated just below the boiling point of benzene for about 2 hours and was then distilled again until the volume was about one-half of that originally present (250 ml.) The above process was repeated once more except that the volume was reduced to one-third of the original volume (167 ml.). The reaction mixture was then cooled and filtered. The filter cake consisted of dl-4-acetamido-2-dimethylaminomethylenecyclohexanone formed in the above reaction; weight=6.45 g. Evaporation of the filtrate to dryness yielded a residue, chromatography of a chloroform solution of which over 200 g. of Florisil using chloroform containing increasing amounts of methanol (0–5%) as an eluant, yielded more dl-4-acetamido-2-dimethylaminomethylenecyclohexanone;
M.P.=132°–133° C. (from benzene); yield=5.55 g.; total yield=12 g.

Analysis Calc.: C, 62.83; H, 8.63; N, 13.32; Found: C, 63.07; H, 8.38; N, 13.12.

Potassium glycinate was prepared by reacting 9 g. of glycine and 6.7 g. of potassium hydroxide in 400 ml. of anhydrous ethanol. 22.6 g. of dl-4-acetamido-2-dimethylaminomethylenecyclohexanone were added thereto and the resulting mixture heated to refluxing temperature under a nitrogen atmosphere for 1.75 hours. The reaction mixture was cooled, diluted with ether, and filtered. The filter cake, which weighed 28.7 g., was added to 400 ml. of acetic anhydride and the resulting mixture heated to reflux temperature under a nitrogen atmosphere for one hour. The reaction mixture was cooled and the volatile constituents removed by evaporation in vacuo. The resulting residue was suspended in chloroform and filtered. The filtrate was chromatographed over 350 g. of Florisil, using chloroform containing increasing amounts (0–2%) of methanol as the eluant. Fractions shown by TLC to contain dl-2-acetyl-5-acetamido-4,5,6,7-tetrahydro-2H-benzo[c]pyrrole formed in the above reaction were combined and the solvent evaporated therefrom. Crystallization of the residue from ether yielded purified dl-2-acetyl-5-acetamido-4,5,6,7-tetrahydro-2H-benzo[c]pyrrole melting at 151°–153° C.; yield=17.7 g.

Analysis Calc.: C, 65.43; H, 7.32; N, 12.72; Found: C, 65.72; H, 7.34; N, 12.45.

A hydrolysis mixture was prepared from 5.1 g. of dl-2-acetyl-5-acetamido-4,5,6,7-tetrahydro-2H-benzo[c]pyrrole, 50 g. of sodium hydroxide, 50 ml. of water, and 200 ml. of ethanol. The mixture was heated to refluxing temperature under a nitrogen atmosphere for about 16 hours and was then cooled. The cooled mixture was diluted with water. The alkaline aqueous mixture was extracted several times with methylene dichloride, the methylene dichloride extracts were combined and the combined extracts washed with saturated aqueous sodium chloride and dried. Evaporation of the solvent therefrom yielded a residue comprising dl-5-amino-4,5,6,7-tetrahydro-2H-benzo[c]pyrrol formed in the above reaction. A chloroform solution of the residue was filtered through 105 g. of alumina (grade II). Concentration of the resulting filtrate yielded 2.52 g. of a yellow solid comprising dl-5-amino-4,5,6,7-tetrahydro-2H-benzo[c]pyrrole.

EXAMPLE 2

PREPARATION OF DL-5-DIETHYLAMINO-4,5,6,7-TETRAHYDRO-2H-BENZO[c]PYRROLE

A solution was prepared by adding 2.52 g. of dl-5-amino-4,5,6,7-tetrahydro-2H-benzo[c]pyrrole to 100 ml. of methanol. 1.2 g. of sodium cyanoborohydride were added followed by 6 ml. of acetaldehyde. The reaction mixture was stirred at ambient temperature under nitrogen atmosphere for about 16 hours, and was then diluted with aqueous sodium bicarbonate. The aqueous layer was extracted with chloroform, and the chloroform extract separated and washed with saturated aqueous sodium chloride. The chloroform solution was then dried and the solvent removed therefrom by evaporation. The resulting residue was redissolved in chloroform and the chloroform solution chromatographed over 35 g. of Florisil using chloroform containing increasing amounts (2-4%) methanol as the eluant. By combining fractions shown by TLC to contain a material different than starting material, 1.84 g. of solid were obtained which was rechromatographed over Florisil. Combining fractions shown to contain dl-5-diethylamino-4,5,6,7-tetrahydro-2H-benzo[c]pyrrole by TLC followed by evaporation of the solvent from the combined fractions in vacuo yielded a residue weighing 0.66 g. The residue was dissolved in ether and treated with an excess of an etheral solution of maleic acid. dl-5-diethylamino-4,5,6,7-tetrahydro-2H-benzo[c]pyrrole maleate thus prepared was recrystallized from a methanol-ether solvent mixture to yield purified compound melting at 81°-83° C.; yield=385 mg.

Analysis Calc.: C, 62.32; H, 7.84; N, 9.08; Found: C, 62.37; H, 7.57; N, 8.94.

Following the above procedure but substituting propionaldehyde for acetaldehyde, dl-5-di-n-propylamino-4,5,6,7-tetrahydro-2H-benzo[c]pyrrole maleate was prepared, melting at 134°-136° C. after recrystallization from an isopropanol-ether solvent mixture.

Analysis Calc: C, 64.26; H, 8.39; N, 8.33; Found: C, 64.32; H, 8.68; N, 8.17.

EXAMPLE 3

PREPARATION of DL-2-METHYL-5-DI-n-PROPYLAMINO-4,5,6,7-TETRAHYDROISOINDOLE 2 millimoles (680 mg) of dl-5-di(n-propyl)amino 4,5,6,7-tetrahydro-2H-benzo[c]pyrrole were dissolved in 75 ml. of dimethylacetamide (DMA). 10 millimoles (1.1 g) potassium tertiary-butoxide were added and the resulting mixture stirred for 20 minutes under nitrogen. Next, a solution of 2.1 millimoles of methyl iodide (0.13 ml) in 5 ml. of DMA was added in dropwise fashion. The resulting reaction mixture was stirred at ambient temperature for 5 hours at which time an additional 0.13 ml of methyl iodide was added and the subsequent mixture stirred for an additional 3.5 hours. The reaction mixture was then diluted with water and the aqueous layer extracted with ethyl acetate. The ethyl acetate layer was separated and washed with water followed by saturated aqueous sodium chloride. The ethyl acetate layer was then dried and the ethyl acetate removed therefrom by evaporation. An ether solution of the resulting residue was chromatographed over 35 g. of Florisil using ether as the eluant. Fractions shown by TLC to contain dl-2-methyl-5-di-n-propylamino-4,5,6,7-2H-benzo[c]pyrrole were combined and the solvent removed therefrom in vacuo. NMR of the residue thus obtained indicated that the dl-2-methyl-5-di-n-propylamino-4,5,6,7-tetrahydro-2H-benzo[c]pyrrole had been prepared.

EXAMPLE 4

PREPARATION of DL-5-ACETAMIDO-4,5,6,7-TETRAHYDRO-2H-BENZO[c]PYRROLE

To a solution of 6.7 g. of 4-acetamidocyclohexanone [prepared by the method of Fraser and Swingle, *Can. J. Chem.*, 48, 2065 (1970)], in 150 ml. of anhydrous ethanol were added 25 ml. of ethyl orthoformate containing a few crystals of p-toluenesulfonic acid monohydrate. The reaction mixture was stirred at ambient temperature for about 16 hours, after which time the volatile constituents were removed by evaporation in vacuo. The residue comprising the diethylketal was dissolved in 200 ml. of toluene and the toluene was removed by distillation under a nitrogen atmosphere, until all of the diethylketal had been converted to the 1-ethoxycyclohexene derivative. The solution was cooled, washed with aqueous sodium bicarbonate and dried. Evaporation of the toluene yielded a residue comprising 4-acetamido-1-ethoxycyclohexene melting at 100°-102° C. after recrystallization from an ether-hexane solvent mixture; yield=6.2 g.

A solution of 3 g. of 4-acetamido-1-ethoxycyclohexene in 40 ml. of dioxane was added slowly to a solution of 3.2 g. of 1,2,4,5-tetrazine dicarboxylic ester [prepared by the method of Sauer, et al., *Chem. Ber.*, 98, 1435 (1965)] in 100 ml. of dioxane. The reaction mixture was stirred at ambient temperature for about 3 days after which time TLC indicated one major spot with several minor spots present. The reaction mixture was evaporated in vacuo, the resulting residue dissolved in chloroform, and the chloroform solution chromatographed over 200 g. of Florisil using chloroform containing increasing amounts (2-5%) of methanol as the eluant. Fractions shown to contain a single major spot material by TLC were combined and the solvent removed from the combined fractions in vacuo. The residue was crystallized by triturating with ether; mp=137°-139° C.; yield=3.21 g. Recrystallization of the residue from the ethermethanol solvent mixture yielded purified dl-6-acetamido-1,4-di(carbomethoxy)-5,6,7,8-tetrahydrobenzo[d]pyridazine melting at 143°-144° C.

Analysis Calc.: C, 54.72; H, 5.58; N, 13.67; Found: C, 54.75; H, 5.64; N, 13.49.

A solution was prepared by adding 2.59 g. of dl-6-acetamido-1,4-di(carbomethoxy)-5,6,7,8-tetrahydrobenzo[d]pyridazine to 100 ml. of glacial acetic acid. 5 g. of zinc dust were added and the resulting mixture stirred at ambient temperature for about 1 day. An additional 5 g. of zinc dust were added after 6 hours. The reaction mixture was then filtered to remove unreacted zinc dust and the resulting filtrate poured over ice. The filtrate was made basic with 14 N aqueous ammonium hydroxide and the alkaline mixture extracted several times with a chloroform-isopropanol solvent combination. The organic extracts were separated and combined, and the combined extracts washed with saturated aqueous sodium chloride and then dried. Evaporation of the solvent therefrom yielded dl-5-acetamido-1,3-di(carbomethoxy)-4,5,6,7-tetrahydro-2H-benzo[c]pyrrole formed in the above reaction; yield = 1.83 g. Recrystallization from methanol yielded crystalline material melting at 231°–232° C.

Analysis Calc.: C, 57.14; H, 6.16; N, 9.52; Found: C, 57.05; H, 5.99; N, 9.26.

A reaction mixture was prepared containing 1.8 g. of dl-5-acetamido-1,3-di(carbomethoxy)-4,5,6,7-tetrahydro-2H-benzo[c]pyrrole, 80 ml. of THF and 20 ml. of 2 N aqueous sodium hydroxide. The reaction mixture was heated to refluxing temperature under a nitrogen atmosphere for about 3 hours after which time it was cooled and the volatile constituents evaporated therefrom in vacuo. The residue was dissolved in 25 ml. of water and the aqueous solution made acidic by the addition of 1 N aqueous hydrochloric acid. The diacid, dl-5-acetamido-1,3-dicarboxy-4,5,6,7-tetrahydro-2H-benzo[c]pyrrole, formed in the above hydrolysis being insoluble in the acidic layer precipitated and was collected by filtration. Recrystallization from a benzene-methanol solvent mixture yielded crystalline diacid melting at 233°–235° C. with decomposition.

Analysis Calc.: C, 54.13; H, 5.30; N, 10.52; Found: C, 53.90; H, 5.37; N, 10.45.

A reaction mixture, prepared from 850 mg. of dl-5-acetamido-1,3-dicarboxy-4,5,6,7-tetrahydro-2H-benzo[c]pyrrole, 50 mg. of copper powder and 25 ml. of quinoline, was heated to 200° C. under a nitrogen atmosphere. Gas evolution was noticable as the temperature approached 150° C. Heating in the range 200°–210° C. was carried on for 15 minutes after which time the reaction mixture was poured over ice. The resulting aqueous mixture was extracted with chloroform, and the chloroform extract was separated, washed with 0.1 N aqueous hydrochloric acid, 10 percent aqueous sodium hydroxide and finally water. The chloroform was removed therefrom by evaporation in vacuo to yield 0.26 g. of a dark oil as a residue. Chromatography over 15 g. of Florisil using chloroform containing from 0 to 1 percent methanol as the eluant yielded 40 mg. of dl-5-acetamido-4,5,6,7-tetrahydro-2H-benzo[c]pyrrole. The product was identical to the compound prepared by deacetylation of dl-5-acetamido-2-acetyl-4,5,6,7-tetrahydro-2H-benzo[c]pyrrole from Example 1.

As evidence of the utility of the compounds of this invention in the treatment of Parkinson's Syndrome, it has been found that they affect turning behavior in a test procedure utilizing 6-hydroxydopamine-lesioned rats. In this test, nigro-neostriatal-lesioned rats are employed prepared by the procedure of Ungerstedt and Arbuthnott, *Brain Res*, 24, 485 (1970). A compound having dopamine agonist activity upon injection causes the rats to turn in circles contralateral to the side of the lesion. After a latency period, which varies from compound to compound, the number of turns is counted over a 15-minute period. The compounds are dissolved in water and the aqueous solution injected into the rat by the intraperitoneal route at a dose level of 1 mg/kg. dl-5-Di(n-propyl)amino-4,5,6,7-tetrahydro-2H-benzo[c]pyrrole maleate gave an average of 34 turns per rat with ⅓ of the rats exhibiting turning behavior in the above test.

The compounds of this invention are also useful as prolactin inhibitors and as such can be employed in the treatment of inappropriate lactation, such as postpartum lactation, and of galactorrhea. As evidence of their utility in the treatment of diseases in which it is desirable to reduce the mammalian prolactin level, the compounds of this invention have been shown to inhibit prolactin according to the following procedure.

Adult male rats of the Sprague-Dawley strain weighing about 200 g. were housed in an air-conditioned room with controlled lighting (lights on 6 a.m.–8 p.m.) and fed lab chow and water ad libitum. Each rat received an intraperitoneal injection of 2.0 mg. of reserpine in aqueous suspension 18 hours before administration of the isoindole. The purpose of the reserpine was to keep prolactin levels uniformly elevated. The compounds under test were dissolved in water and were injected intraperitoneally at doses ranging from 5 mg/kg down to 50 mcg/kg. Each compound was administered at each dose level to a group of 10 rats, and a control group of 10 intact males received an equivalent amount of solvent. One hour after treatment all rats were killed by decapitation, and 150 μl aliquots of serum were assayed for prolactin.

The difference between the prolactin level of the treated rats and prolactin level of the control rats divided by the prolactin level of the control rats gives the percent inhibition of prolactin secretion attributable to the compounds of this invention. These inhibition percentages are given in Table 1 below. In the table, column 1 gives the name of the compound; and columns 2–4 the percent prolactin inhibition at the given dose level.

TABLE 1

| Name of Compound | Percent Inhibition of Prolactin at a Given Dose Level | | |
|---|---|---|---|
| | 5 mg/kg | 500 mcg/kg | 50 mcg/kg |
| dl-5-di-(n-propyl)amino-4,5,6,7-tetrahydro-2H-benzo[c]pyrrole maleate | 91 | 47 | 20 |
| dl-5-diethylamino-4,5,6,7-tetrahydro-2H-benzo[c]pyrrole maleate | 23 | 25 | — |

In using the compounds of this invention to inhibit prolactin secretion or to treat Prakinson's syndrome or for other pharmacologic action, a pharmaceutically active compound according to Formula I above, or a salt thereof with a pharmaceutically-acceptable acid, is administered to a subject suffering from Parkinsonism or in need of having their prolactin level reduced in an amount effective to alleviate some of the symptoms of Parkinsonism or to reduce an elevated prolactin level. Oral administration is preferred. If parenteral administration is used, the injection is preferably by the subcutaneous route using an appropriate pharmaceutical formulation. Other modes of parenteral administration such as intraperitoneal, intramuscular, or intravenous routes are equally effective. In particular, with intravenous or intramuscular administration, a water soluble pharmaceutically-acceptable salt is employed. For oral administration, a pharmaceutically active compound according to Formula I either as the free base or in the form of a salt thereof can also be mixed with standard pharmaceutical excipients and loaded into empty telescoping gelatin capsules or pressed into tablets. The oral dosage range is from about 0.01 to 10 mg/kg of mammalian weight and the parenteral dose range from about 0.0025 to 2.5 mg/kg of mammalian weight. Intraperitoneal dosages of 10–30 mg/kg of dl-5-di(n-propyl)amino-4,5,6,7-tetrahydrobenzo[2H]pyrrole maleate in the mouse resulted in no deaths but dosages of 100–300 mg/kg were fatal. Some toxic side effects were observed at the 30 mg/kg dose level.

We claim:

1. A compound of the formula

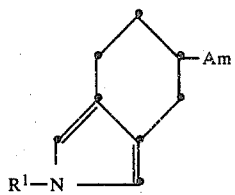

wherein
$R^1$ is H, $R^2$ or

Am is $NH_2$ or $N(R^2)_2$;
$R^3$ is methyl, ethyl or n-propyl; and each $R^2$ is independently $R^3$ or allyl; except that $R^1$ is not

when Am is $NH_2$ and acid addition salts thereof.

2. A dopamine agonist compound according to claim 1 wherein $R^1$ is H or $R^2$; Am is $N(R^2)_2$; and $R^2$ is allyl, methyl, ethyl or n-propyl; and pharmaceutically-acceptable acid addition salts thereof.

3. A compound according to claim 1 wherein $R^1$ is H or $R^2$; Am is $NH_2$; and $R^2$ is methyl, allyl, ethyl or n-propyl and acid addition salts thereof.

4. A compound according to claim 2, said compound being dl-5-di(n-propyl)amino-4,5,6,7-tetrahydro-2H-benzo[c]pyrrole.

5. A compound according to claim 2, said compound being dl-5-diethylamino-4,5,6,7-tetrahydro-2H-benzo[c]pyrrole.

6. A compound according to claim 3 said compound being dl-5-amino-4,5,6,7,-tetrahydro-2H-benzo[c]pyrrole.

7. A compound according to claim 3 in which $R^1$ is acetyl and Am is $NH_2$, and acid addition salts thereof.

8. A compound of the formula

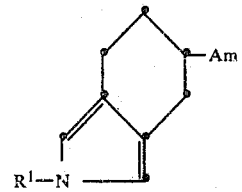

wherein
$R^1$ is H, $R^2$ or

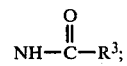

Am is

and
$R^3$ is methyl, ethyl or n-propyl; and $R^2$ is $R^3$ or allyl.

9. A compound according to claim 8 in which $R^1$ is acetyl and Am is

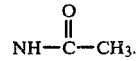

* * * * *